US00PP15736P2

(12) United States Plant Patent
Lim

(10) Patent No.: US PP15,736 P2
(45) Date of Patent: Apr. 26, 2005

(54) SHRUB ROSE PLANT NAMED 'BAIEAM'

(50) Latin Name: *Rosa hybrida*
Varietal Denomination: BAIeam

(75) Inventor: Peter P. Lim, Yamhill, OR (US)

(73) Assignee: Bailey Nurseries, Inc., St. Paul, MN (US)

( * ) Notice: Subject to any disclaimer, the term of this patent is extended or adjusted under 35 U.S.C. 154(b) by 39 days.

(21) Appl. No.: 10/769,749

(22) Filed: Feb. 3, 2004

(51) Int. Cl.[7] ..... A01H 5/00
(52) U.S. Cl. ..... Plt./107
(58) Field of Search ..... Plt./107

*Primary Examiner*—Anne Marie Grunberg
*Assistant Examiner*—Annette H Para
(74) *Attorney, Agent, or Firm*—Burns, Doane, Swecker & Mathis, LLP

(57) ABSTRACT

A new and distinct variety of landscape shrub rose plant is provided which abundantly forms on a continuous basis attractive semi-double rich fuschia blended with dark pink blossoms. The blossoms also display a slight sweet rose fragrance. The plant exhibits a compact and bushy growth habit, attractive glossy dark green foliage that initially bears a tint of red-purple, and good tolerance to Black Spot and Powdery Mildew. The attractive dark green foliage contrasts nicely with the blossom coloration. The new variety is particularly well suited for growing as attractive ornamentation in parks and gardens.

1 Drawing Sheet

Botanical commercial classification: *Rosa hybrida*/Shrub Rose Plant.
Varietal denomination: cv. 'BAIeam'.

SUMMARY OF THE INVENTION

The new variety of *Rosa hybrida* landscape shrub rose plant was created at Yamhill, Oreg. during 1994 by artificial pollination wherein two parents were crossed which previously had been studied in the hope that they would contribute the desired characteristics. The female parent (i.e., the seed parent) was the hybrid *Rosa kordesii* 'INTerlav' variety (U.S. Plant Pat. No. 5,916). The 'INTerlav' variety is marketed under the LAVENDER DREAM trademark. The male parent (i.e., the pollen parent) was the 'Henry Kelsey' variety (non-patented in the United States). The 'Henry Kelsey' originated at the Morden Research Station, Winnepeg, Canada. The parentage of the new variety can be summarized as follows:

'INTerlav'×'Henry Kelsey'.

The seeds resulting from the above pollination were sown and plants were obtained which were physically and biologically different from each other. Selective study resulted in the identification during 1996 of a single plant of the new variety having the distinctive ornamental characteristics hereafter described.

It was found that the new variety of the present invention:

(a) exhibits a compact and bushy growth habit, (b) abundantly forms on a continuous basis in clusters attractive semi-double rich fuschia blended with dark pink blossoms, (c) forms attractive glossy dark green foliage when mature that initially bears a tint of red-purple, (d) displays excellent tolerance to Black Spot and Powdery Mildew; and (e) is particularly well suited for growing as attractive ornamentation in parks and gardens.

The young red-purple flower buds open to rich fushia blended with dark pink blooms that fade to medium pink. The aging petals commonly detach cleanly and do not detract from the attractiveness of the blooms. The new variety is a tough shrub rose with good hardiness.

The new variety well meets the needs of the horticultural industry and can be grown to advantage in the landscape where attractive ornamentation is desired. The distinctive blossoms are displayed throughout the season. The plant can be grown as a specimen or as a mass planting.

The new variety can be readily distinguished from its ancestors. For instance, the blossoms of the 'INTerlav' variety are deep lilac pink and the blossoms of the 'Henry Kelsey' variety are medium red in coloration.

The new variety also can be readily distinguished from the 'SPEvu' variety (non-patented in the United States) and the 'Meipoque' variety (U.S. Plant Pat. No. 5,956). More specifically, the 'SPEvu' variety commonly achieves a greater height of approximately 80 cm at the end of the growing season, and forms double deep pink blossoms having a greater diameter of approximately 3 cm. Also, the 'Meipoque' variety commonly assumes a greater height of approximately 1.5 m at the end of the growing season and forms much larger blossoms having a diameter of approximately 5 cm that are medium pink with a white eye on the obverse and medium pink on the reverse.

The new variety has been found to undergo asexual propagation by budding on an understock and by the rooting of cuttings. 'Dr. Huey' rootstock was used during the budding. Such asexual propagation by these techniques at Yamhill, Oreg., St. Paul, Minn., and at Phoenix, Ariz. has shown that the characteristics of the new variety are stable and are strictly transmissible by such asexual propagation from one generation to another. The new variety grows well on its own roots.

Initially the new plant was designated 94A922-1L. The new variety subsequently has been named the 'BAIeam' variety, and currently is being marketed while using the DAYDREAM trademark.

BRIEF DESCRIPTION OF THE PHOTOGRAPHS

The accompanying photographs show as nearly true as it is reasonably possible to make the same in a color illustrations of this character, typical specimens of the new variety. The rose plants of the new variety had been propagated by the rooting of cuttings, were approximately two and three years of age, and were being grown outdoors at St. Paul, Minn. and at Yamhill, Oreg.

DETAILED DESCRIPTION

Figure 1:
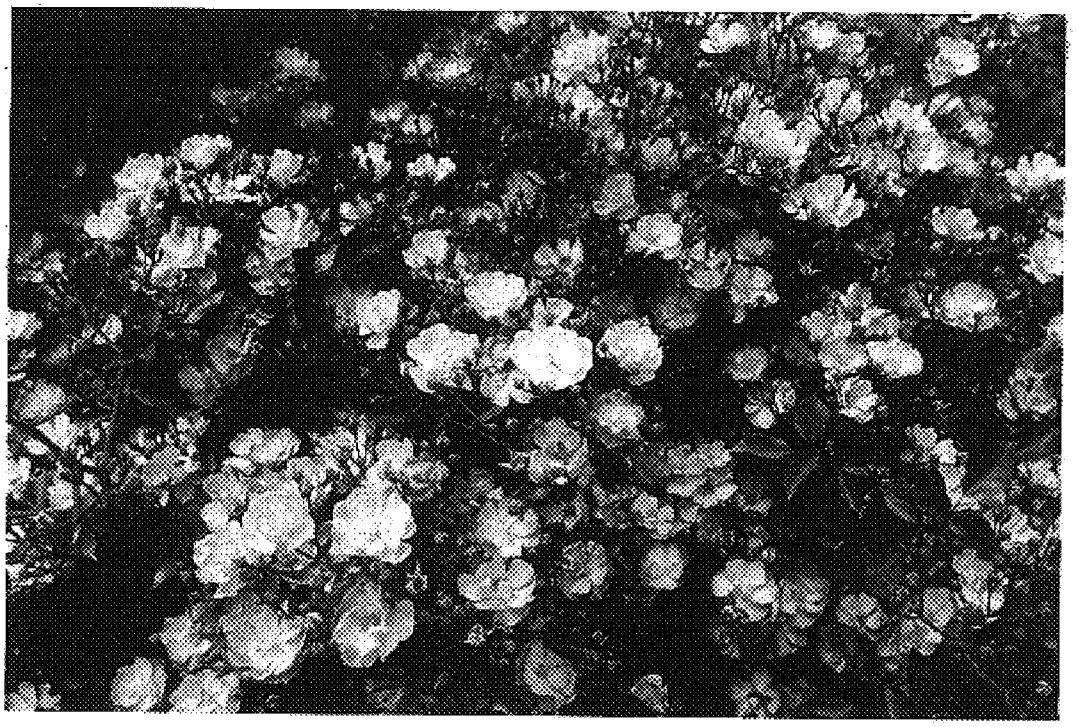
FIG. 1 illustrates typical blossoms in various stages of opening and foliage of the new variety. Clusters of attractive semi-double rich fuschia blended with dark pink blossoms are shown.
Figure 2:
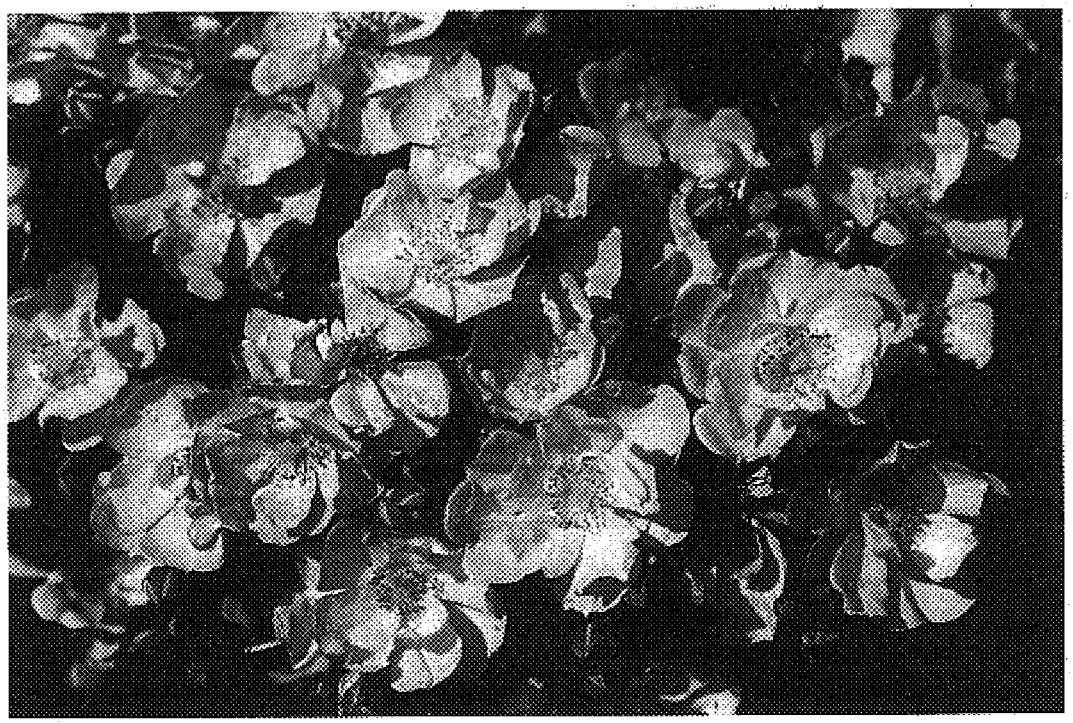
FIG. 2 illustrates a close view typical fully open flowers of the new variety.

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June and July 2002 and 2003 at St. Paul, Minn., and May 2003 at Phoenix, Ariz.

Botanical classification: *Rosa hybrida,* var. 'BAIeam'.
Class: Landscape Shrub.
Plant:
- *Height.*—Approximately 60 cm on average at the end of the growing season.
- *Width.*—Approximately 90 cm on average at the end of the growing season.
- *Habit.*—Compact, rounded, and bushy.

Branches:
- *Color.*—Young stems: Yellow-Green Group 144A. Adult wood: Commonly between Yellow-Green Group 146B and 146C with highlights of Greyed-Purple Group 184A.
- *Thorns.*—Size: Smaller bristles/prickles with some thorns of approximately 0.25 cm in length on average. Bearing the smaller bristles/prickles and thorns are more common on younger stems, and there commonly are few or no thorns on most adult branches. Color: Greyed-Purple Group 187B.

Leaves:
- *Stipules.*—Generally parallel with the auricle facing outward.
- *Petioles.*—Upper surface: Yellow-Green Group 147A. Under surface: Yellow-Green Group 146C and tinted with Greyed-Purple Group 184A and 184B.
- *Leaflets.*—Number: 3,5 (most often), and 7. Shape: ovate with a rounded base and an acuminate tip. Serration: serrulate. Texture: bears a glossy finish. General appearance: dark green with a glossy surface when mature. color (young foliage): Upper surface: Yellow-Green Group 146A and 146B with highlights of Greyed-Purple Group 184A. Under surface: Yellow-Green Group 146B with highlights of Greyed-Purple Group 184A. Color: (adult foliage): Upper surface: Yellow-Green Group 147A. Under surface: Yellow-Green Group 147B with highlights of Greyed-Purple Group 184B.

Inflorescence:
- *Number of flowers.*—Commonly approximately 12 blooms on average per cluster.
- *Peduncle.*—Yellow-Green Group 144A and 144B with highlights of Greyed-Purple Group 184A in coloration, and the length is approximately 2.25 cm on average.
- *Sepals.*—Upper surface: commonly Green Group 143C with stripe of Greyed-Purple Group 184C in coloration. Under surface: Yellow-Green Group 148C with some pubescence. Size: approximately 10 mm in length.
- *Buds.*—Shape: generally rounded. Size: small. Length: approximately 1.0 cm on average. Diameter: approximately 0.5 cm on average. Color: Upper surface: blend of Red-Purple Group 60B and 60C. Under surface: blend of Red-Purple Group 60A and 60B. Basal petal spot: Green-White Group 157A.
- *Flower.*—Shape: semi-double and somewhat informal. Diameter: approximately 2.5 cm on average. Color (when opening begins): Upper surface: Red-Purple Group 64B blending with Red-Purple Group 64D. Under surface: Red-Purple Group 64A blending with Red-Purple Group 64C. Color (when blooming): Upper surface: Red-Purple Group 67C blending with Red-Purple Group 67D. Under surface: Red-Purple Group 64C blending with Red-Purple Group 63D. Color (at end of blooming): Upper surface: Red-Purple Group 73D blending with Red-Purple Group 73D and 75D. uUder surface: Red-Purple Group 64D blending with Red-Purple Group 70C. Color (basal petal spot): Green-White Group 157B. Fragrance: slight sweet rose. Lasting quality: the blossoms commonly last approximately 3 to 5 days on average depending upon the temperature and sunlight exposure. Petal number: approximately 11 on average under normal growing conditions. Petal shape: wedge-shaped commonly with a curled apex when fully open. Petal drop: commonly the petals detach cleanly at full blossom maturity. Anthers: Greyed-Orange Group 163A in coloration. Filament number: commonly approximately 45 on average. Filament color: Yellow Group 11A in coloration. Pistils: approximately 21 on average. Stigmas: Greyed-Orange Group 165C in coloration. Styles: Greyed-Orange Group 165C in coloration. Receptacle: separate and free with achenes at the bottom and center. Hip shape: ovoid. Hip size: approximately 10 mm in length and approximately 8 mm in width. Seeds: dark brown in coloration and approximately 3 mm in length.

Development:
- *Vegetation.*—Vigorous, and compact.
- *Blooming.*—Abundant on strong canes and continuous throughout the season.
- *Resistance to diseases.*—Excellent tolerance to Black Spot, and Powdery Mildew.
- *Hardiness zone.*—U.S.D.A. Hardiness Zone Nos. 4 to 7.

I claim:

1. A new and distinct variety of landscape shrub rose plant characterized by the following combination of characteristics:

(a) exhibits a compact and bushy growth habit, (b) abundantly forms on a continuous basis in clusters attractive semi-double rich fuschia blended with dark pink blossoms, (c) forms attractive glossy dark green foliage when mature that initially bears a tint of red-purple, (d) displays excellent tolerance to Black Spot and Powdery Mildew, and (e) is particularly well suited for growing as attractive ornamentation in parks and gardens;

substantially as herein shown and described.

* * * * *